(12) United States Patent
Chin

(10) Patent No.: US 10,112,035 B2
(45) Date of Patent: Oct. 30, 2018

(54) CATHETER WITH VESSEL LINING AND METHODS FOR USING SAME

(71) Applicant: Cruzar Medsystems, Inc., Braintree, MA (US)

(72) Inventor: Albert K. Chin, Palo Alto, CA (US)

(73) Assignee: Cruzar Medsystems, Inc., Braintree, MA (US)

(*) Notice: Subject to any disclaimer, the term of this patent is extended or adjusted under 35 U.S.C. 154(b) by 218 days.

(21) Appl. No.: 14/559,259

(22) Filed: Dec. 3, 2014

(65) Prior Publication Data

US 2015/0088187 A1    Mar. 26, 2015

Related U.S. Application Data

(62) Division of application No. 13/267,657, filed on Oct. 6, 2011, now Pat. No. 8,926,559.

(Continued)

(51) Int. Cl.

| | | |
|---|---|---|
| *A61M 1/00* | (2006.01) | |
| *A61M 25/10* | (2013.01) | |
| *A61B 1/00* | (2006.01) | |
| *A61M 25/06* | (2006.01) | |
| *A61M 25/01* | (2006.01) | |
| *A61B 17/34* | (2006.01) | |

(52) U.S. Cl.
CPC ....... *A61M 25/104* (2013.01); *A61B 1/00151* (2013.01); *A61M 25/0119* (2013.01); *A61M 25/0662* (2013.01); *A61B 2017/3435* (2013.01); *A61M 2025/0681* (2013.01); *A61M 2025/1065* (2013.01); *A61M 2210/12* (2013.01)

(58) Field of Classification Search
CPC ....... A61M 25/0119; A61M 2025/1065; A61B 2017/3435; A61B 1/00151
See application file for complete search history.

(56) References Cited

U.S. PATENT DOCUMENTS

| | | |
|---|---|---|
| 3,669,099 A | 10/1972 | Silverman |
| 3,911,927 A | 10/1975 | Rich et al. |

(Continued)

FOREIGN PATENT DOCUMENTS

| | | |
|---|---|---|
| EP | 0227583 | 7/1987 |
| EP | 0359489 | 3/1990 |

(Continued)

OTHER PUBLICATIONS

European Search Report issued in European Application No. 15178491.5 dated Mar. 18, 2016.

(Continued)

*Primary Examiner* — Nathan R Price
*Assistant Examiner* — Anh Bui
(74) *Attorney, Agent, or Firm* — Greenberg Traurig, LLP; Chinh H. Pham; Todd C. Basile

(57) ABSTRACT

A system for providing access across a site of obstruction is provided. The system may include a sleeve, having a distal portion that can move from an inverted position to an everted position. A balloon situated within the sleeve can be extended so as to evert sleeve. A pathway can extend across a juncture between the distal portion and the remaining portion of the sleeve so as to provide access across the site of obstruction. A method for providing access across the site of obstruction is also provided.

7 Claims, 5 Drawing Sheets

Related U.S. Application Data

(60) Provisional application No. 61/390,301, filed on Oct. 6, 2010.

(56) References Cited

U.S. PATENT DOCUMENTS

| | | | |
|---|---|---|---|
| 4,043,345 A | 8/1977 | Kramann et al. | |
| 4,109,659 A | 8/1978 | Sheridan | |
| 4,243,040 A | 1/1981 | Beecher | |
| 4,254,774 A * | 3/1981 | Boretos | A61M 25/1027 604/271 |
| 4,493,711 A * | 1/1985 | Chin | A61M 25/0119 604/271 |
| 4,630,609 A | 12/1986 | Chin | |
| 4,871,358 A | 10/1989 | Gold | |
| 5,295,960 A | 3/1994 | Aliahmad et al. | |
| 5,458,573 A | 10/1995 | Summers | |
| 6,767,338 B2 | 7/2004 | Hawk et al. | |
| 6,979,290 B2 | 12/2005 | Mourlas et al. | |
| 7,144,407 B1 | 12/2006 | Lasersohn | |
| 7,494,485 B2 | 2/2009 | Beck | |
| 7,794,447 B2 | 9/2010 | Dann et al. | |
| 8,491,519 B2 | 6/2013 | Chin | |
| 8,926,559 B2 | 1/2015 | Chin | |
| 2002/0120226 A1 | 8/2002 | Beck | |
| 2003/0144629 A1 | 7/2003 | Hawk et al. | |
| 2005/0049718 A1 | 3/2005 | Dann et al. | |
| 2007/0083158 A1 | 4/2007 | Hirszowicz et al. | |
| 2011/0213469 A1* | 9/2011 | Chin | A61F 5/0076 623/23.65 |
| 2012/0302996 A1 | 11/2012 | Barash | |
| 2015/0142045 A1 | 5/2015 | Bacich | |

FOREIGN PATENT DOCUMENTS

| | | |
|---|---|---|
| EP | 1494524 | 1/2005 |
| GB | 1482873 | 8/1977 |
| JP | S50-149171 A | 11/1975 |
| JP | S58-500694 A | 5/1983 |
| JP | S59-501149 A | 7/1984 |
| WO | 82/03989 A1 | 11/1982 |
| WO | 84/00113 A1 | 1/1984 |
| WO | 2001083017 | 11/2001 |
| WO | 2003/084584 A2 | 10/2003 |
| WO | 2003/084584 A3 | 10/2003 |
| WO | 2011088381 | 7/2011 |
| WO | 2012/048142 A | 4/2012 |

OTHER PUBLICATIONS

International Search Report and Written Opinion for International Application No. PCT/US11/55149 dated Jan. 23, 2012.

Office Action issued for U.S. Appl. No. 13/267,657 dated Oct. 9, 2012.

Extended European Search Report issued for European Application No. 11831621.5 dated Feb. 26, 2014.

Office Action issued for U.S. Appl. No. 14/073,270 dated Jan. 16, 2015.

Partial European Search Report issued in European Application No. 15178491.5 dated Dec. 21, 2015.

International Search Report in International Application No. PCT/US2017/059972 dated Feb. 28, 2018.

* cited by examiner

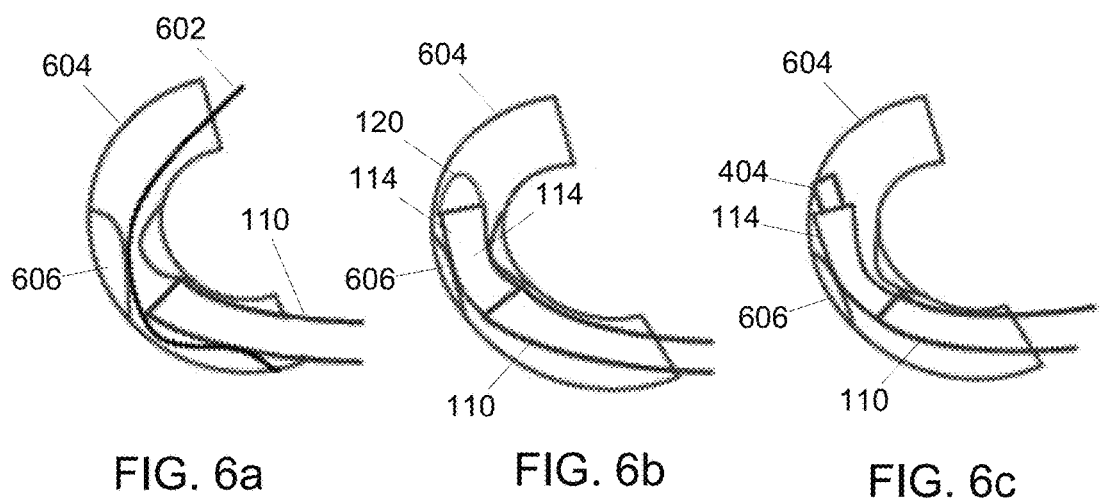

CATHETER WITH VESSEL LINING AND METHODS FOR USING SAME

RELATED APPLICATIONS

This application is a divisional application of U.S. application Ser. No. 13/267,657, filed on Oct. 6, 2011, which claims priority to and the benefit of U.S. Provisional Application No. 61/390,301 (filed Oct. 6, 2010), each of which is incorporated herein by reference in its entirety.

BACKGROUND

Obstructions within body cavities and vessels can often inhibit access through the cavities and vessels. For example, atherosclerosis and other circulatory diseases occur when the arteries become narrowed or blocked. Plaque formation within the arteries can cause bump or other obstructions on the artery wall. Similarly, clots, thrombus, stenosis, or tortuosity in a vessel can also act to inhibit access or movement through the vessel.

Such an obstruction can also cause health problems by impeding movement of fluid through the vessel. For example, if the vessel is a blood vessel, the obstruction may impede blood flow.

In addition, the ability of the obstruction to block the vessel can also create issues during surgery. For example, during a surgical procedure (e.g., angioplasty, stent placement, or other procedures within a cavity or vessel) a surgeon may require access, along the vessel, to a site distal to the obstruction. In other situations, a surgeon may wish to deliver a stent, catheter, or other device to the site of obstruction so that fluid, surgical devices, and/or other material can move across the obstruction. However, it can often be difficult to pass a catheter or other devices across the area of obstruction in the presence of an obstruction in the vessel. Repeated attempts and increased advancement force can be dangerous, as such acts may result in vessel perforation or laceration.

Accordingly, it would be desirable to have a system that can provide access across an obstruction in a vessel in order to provide easier passage through the vessel while minimizing potential damage to the vessel walls.

SUMMARY OF THE INVENTION

A system for providing access across a site of obstruction is provided. The system may include a sleeve, having a distal portion that can move from an inverted position to an everted position. A balloon situated within the sleeve can be extended so as to evert sleeve. A pathway can extend across a juncture between the distal portion and the remaining portion of the sleeve so as to provide access across the site of obstruction.

A method for providing access across a site of obstruction is also provided. The method includes positioning an inverted, distal portion of a sleeve adjacent to a site of obstruction. The distal portion may be moved from an inverted position to an everted position so that the distal portion extends across the site of obstruction thereafter. A pathway, extending across a juncture between the distal portion and the remainder of the sleeve, is provided to allow access across the site of obstruction.

BRIEF DESCRIPTION OF DRAWINGS

FIGS. 6a-6c illustrate a system for providing access across an area of obstruction in accordance with an embodiment of the present invention.

DETAILED DESCRIPTION

In accordance with various embodiments of the present invention, systems and methods are provided for providing access across an obstruction, such as an obstruction observed in connection with a complete or partial blockage within a vessel caused by, for instance, a clot, stenosis, or tortuosity within a blood vessel. The systems and methods described below may also, in some instances, be used to navigate past difficult regions in vessels, including arteries, veins, ureters, urethra, Fallopian tubes, pancreatic ducts, nasal sinuses, or any luminal structures or cavities in the body.

Figure 1:
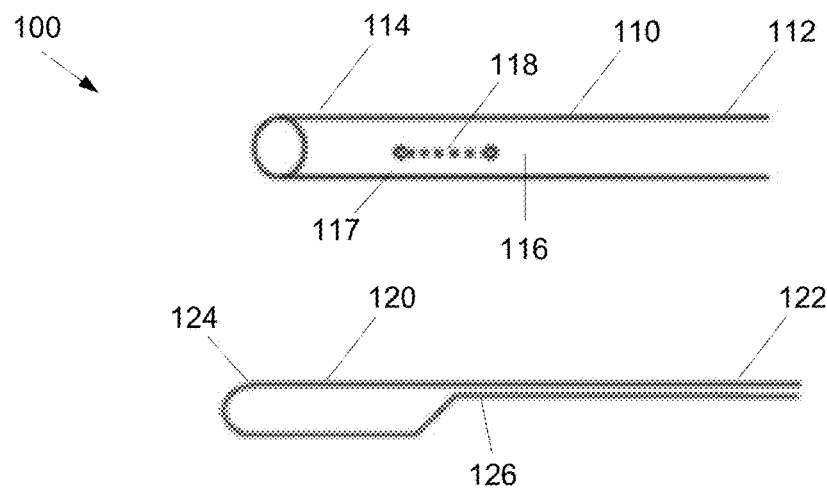
FIG. 1 illustrates various components of a system for providing access across an obstruction in accordance with an embodiment of the present invention.

FIG. 1 shows various components of a system 100 for providing access across an obstruction according to one embodiment of the present invention. System 100, in an embodiment, may include a sleeve 110 and a balloon 120.

The sleeve 110, in an embodiment, can include a proximal portion 112, an opposing distal portion 114, and a pathway 116 therebetween. The pathway 116, as illustrated, may extend across a juncture 117 between distal portion 114 and the remainder of sleeve 110. Also, as will be described, the distal portion 114 of the sleeve 110 may be designed to extend across a site of obstruction to provide access across the obstruction through pathway 116.

As illustrated in FIG. 1, sleeve 110 may be substantially tubular in shape. It should be noted, however, that while described as being tubular in shape, the sleeve 110 may have any other shape desired depending on the particular application, as the shape of the sleeve 110 may aid in the navigation of the sleeve 110 to provide access across a site of obstruction.

In some embodiments, sleeve 110 may be sufficiently flexible so that it can navigate through a tortuous path in a vessel. Additionally or alternatively, sleeve 110 may be sufficiently rigid so that it does not bend or fold in the presence of a proximal force being applied for advancing sleeve 110 through the vessel.

Sleeve 110 may also have any desired length, depending upon the application, so long as sleeve 110 can be advanced through a vessel to the site of obstruction. For example, in one embodiment, sleeve 110 may be relatively long, e.g. a long catheter, so that it can be advanced through a long or tortuous vessel to a site of obstruction. In another embodiment, sleeve 110 may be a relatively short sleeve that can be delivered across the obstruction. The sleeve 110 may also have any diameter sufficient to allow the sleeve 110 to fit within a vessel, depending upon the application and the size of the vessel. In an embodiment, the diameter of the sleeve 110 may remain substantially constant throughout. If desired, the diameter of the sleeve 110 may vary, as necessary, along the length of the sleeve 110.

In one embodiment, the sleeve 110 may further include a coating on an outer surface to reduce friction between the sleeve 110 and the vessel wall upon insertion into the vessel. In one embodiment, the coating may cover the entire outer surface of the sleeve 110. In an alternative embodiment, the coating may be locating only at the distal portion 114. Of course, the coating may be placed onto the outer surface in other manners as well. Likewise, the sleeve 110 may include a coating on an inner surface to reduce friction during eversion. In one embodiment, the inner coating may cover the entire inner surface of the sleeve 110. In an alternative embodiment, the coating may be locating only at the distal portion 114 of the sleeve 110. Of course, the coating may be placed onto the inner surface in other manners as well.

Figure 2A:
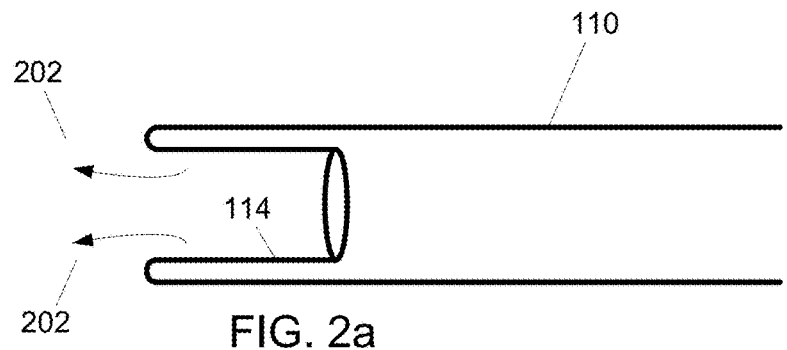
FIG. 2a-2b illustrate a sleeve, used in connection with the system of FIG. 1, for providing access across an obstruction in accordance with an embodiment of the present invention.
Figure 2B:
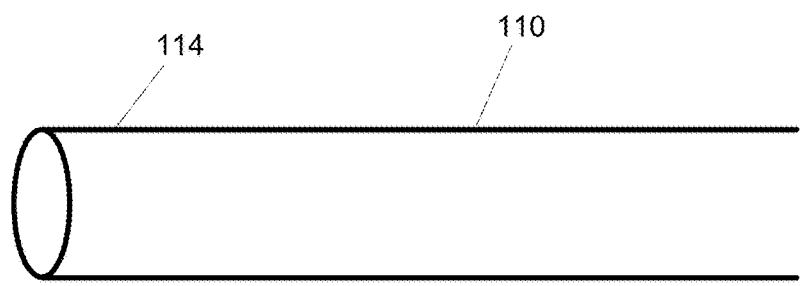

Distal portion 114 of sleeve 110, in an embodiment, may be designed to extend from sleeve 110 across a site of obstruction. In order to extend from sleeve 110, in some embodiments, distal portion 114 may be able to move from an inverted state to an everted state. Looking now at FIG. 2a, in an inverted state, distal portion 114 may be folded into sleeve 110. In this position, the length of sleeve 110 may be relatively shortened. However, during eversion, distal portion 114 may extend from the remainder of sleeve 110 by moving, as shown by arrows 202, from the inverted/folded in position of FIG. 2a, to an everted/extended position shown in FIG. 2b.

By providing a distal portion 114 that can evert in the manner described, distal portion 114 can extend across a site of obstruction to allow access to an area distal to the site. In particular, once distal portion 114 is extended across site, objects and devices, such as catheters, balloon catheters, plaque removal systems, etc., can be advanced through pathway 116 past the site of obstruction. Distal portion 114 of sleeve 110 may also provide protection to the vessel at the site of obstruction so that a device passing through sleeve 110 is less likely to damage the vessel in and around the site of the obstruction.

In order to extend across sites of obstruction that may have different sizes or lengths, distal portion 114 may, in one embodiment, have any desired length, depending upon the application. In one embodiment, distal portion 114 may be relatively long so that it can be everted to extend across a relatively long area of obstruction. In another embodiment, distal portion 114 may be relatively short, if a longer length is not required to provide access across the site of obstruction. Of course, providing a relatively long distal portion 114 within sleeve 110 and subsequently controlling the length or amount of eversion from sleeve 110, across the site of eversion, in order to accommodate the length of the obstruction, is also within the scope of the present invention.

As the distal portion 114 may need to fold, bend, or extend from an inverted state to an everted state, distal portion 114 may, in an embodiment, be made from a material that is sufficiently flexible and pliable to allow such folding, bending, and extending.

In some embodiments, distal portion 114 may be integral with the remainder of sleeve 110. As such, distal portion 114 may be molded or constructed as a single piece along with the remainder of sleeve 110. In other embodiments, distal portion 114 may be a separate piece that can be attached to the remainder of sleeve 110. In such embodiments, distal portion 114 may be attached to the remainder of sleeve 110 in any appropriate fashion, so long as distal portion 114 can be everted from within the remainder of sleeve 110.

In some embodiments, distal portion 114 and the remainder of sleeve 110 may be made from the same material. In other embodiments, distal portion 114 and the remainder of sleeve 110 may be made from different materials. For instance, in one embodiment, if desired, only the distal portion 114 of sleeve 110 may be made from a substantially flexible material that allows eversion, while the remainder of the sleeve 110 may be made from a less flexible material to minimize deformation of the sleeve 110 during delivery through the vessel.

Since the sleeve 110 and distal portion 114 are designed to be inserted into vessels of a human or animal body, the sleeve 110 and/or the distal portion 114, in an embodiment, can be made from a material that is biocompatible. The biocompatibility of the material may help minimize occurrence of adverse reactions due to use of the sleeve 110 within a vessel. Examples of suitable materials include various types of metals, plastics, or any other materials. In some instances, sleeve 110 may also be made from a bioadsorbable material so that sleeve 110 may remain in the body to be absorbed by the body over time.

To deliver the distal portion 114 of sleeve 110 and provide a pathway 116 across an site of obstruction, the system 100 of the present invention may also include a balloon 120 capable of exerting a force on distal portion 114 so as to move the distal portion 114 of sleeve 110 from an inverted position to an everted position. In some embodiments, balloon 120 may be positioned within sleeve 110 so that, as it is inflated, it can push against and evert distal portion 114 from within sleeve 110.

As shown in FIG. 1, the balloon 120, in an embodiment, may include a lumen 126 for inflating and deflating balloon 120. Lumen 126, as can be appreciated, may be a tube, for example, through which fluid can flow for inflating and deflating balloon 120. In some embodiments, lumen 126 may be permanently or detachably coupled to balloon 120.

Lumen 126 may, in one embodiment, be coupled to an inflation mechanism (not shown), that can direct fluid into and out of balloon 120 through lumen 126. The inflation mechanism may be a pump (e.g. a manual or automatic pump), syringe, or other device that can inflate and/or deflate balloon 120 during use. In some embodiments, inflation mechanism may be coupled to an inflation port (not shown), which may in turn be coupled to a proximal end of lumen 126. In another embodiment, inflation port can be situated at another location, such as proximal portion 112 of the sleeve 110. Of course, other locations for the inflation port are possible as long as fluids can enter with a sufficient force to deploy the balloon.

Figure 3A:
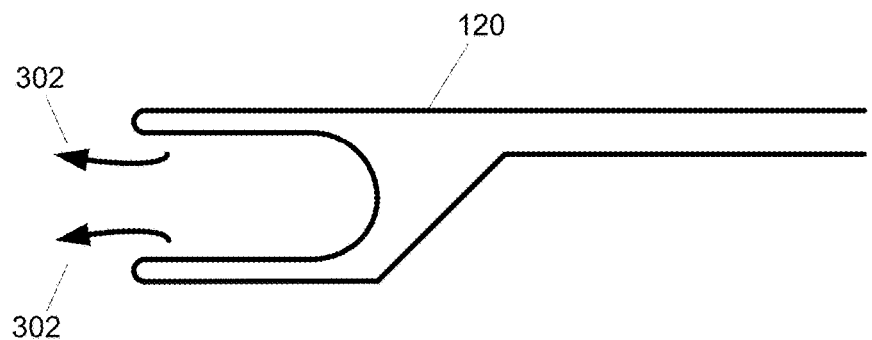
FIGS. 3a-3b illustrate a balloon, used in connection with the system of FIG. 1, for everting the sleeve in FIGS. 2a-2b across an obstruction in accordance with an embodiment of the present invention.
Figure 3B:
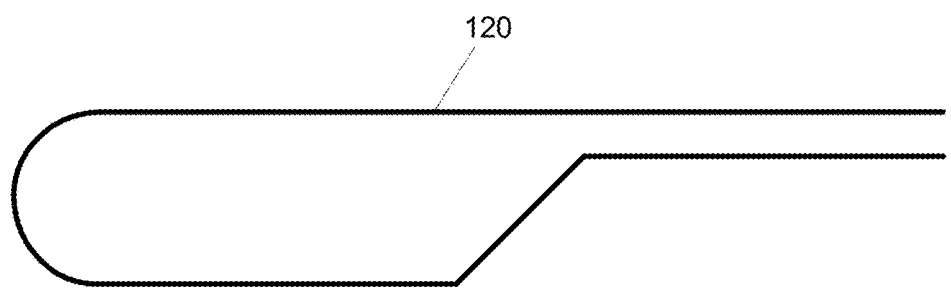

Now looking at FIGS. 3a-b, in order to evert distal portion 114 of sleeve 110, in an embodiment, balloon 120 may be designed to move from a inverted position to an everted position as it is inflated. As shown in FIG. 3a, in the inverted position, the balloon 120 may be inverted and folded into itself. As balloon 120 is inflated, balloon 120 may fill with a fluid (e.g. a liquid or gas) that can evert the distal end of balloon 120 so that balloon 120 extends, as shown by arrows 302, until it reaches a fully extended position, as shown in FIG. 3b. As balloon 120 extends, it may engage the inverted, distal portion 114 of sleeve 110, and act to push the distal portion 114 of sleeve 110 from an inverted position to an everted position. One skilled in the art will recognize that, rather than an inverted position, balloon 120 may also be folded, deflated, or otherwise compressed in other manners so that, once inflated, balloon 120 can push distal portion 114 of sleeve 110 from an inverted state to an everted state.

Figure 4A:
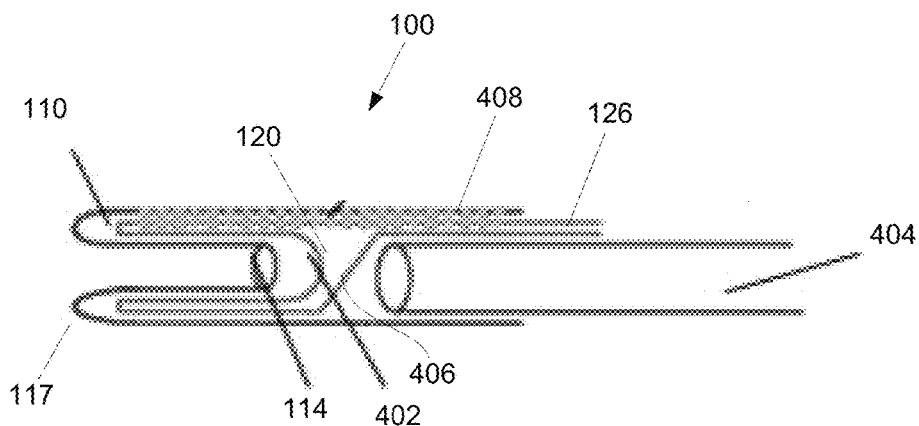
FIGS. 4a-4c illustrate a system for providing access across an area of obstruction in accordance with an embodiment of the present invention.

As shown in FIG. 4a, balloon 120 may be positioned in an inverted state within sleeve 110. In an embodiment, with the balloon 120 in an inverted state, the distal portion 114 of sleeve 110 may be folded into a pocket 402 formed by balloon 120. Folding distal portion 114 into pocket 402 may help to insure that distal portion 114 is properly secured therein for delivery.

It should also be noted that balloon 120, when inflated, may also minimize unwanted movement of sleeve 110 during eversion. For example, as distal portion 114 is everted, it may push against the obstruction and create a backward force, which may tend to push sleeve 110 (and/or balloon 120) backward through the vessel. However, as balloon 120 is inflated, it may press against the inner walls of sleeve 110 and hold the sleeve against the inner walls of the vessel, thus creating static friction between the sleeve and the vessel. The friction can act to anchor sleeve 110 in place so that sleeve 110 can withstand any backpressure without moving.

Figure 4B:
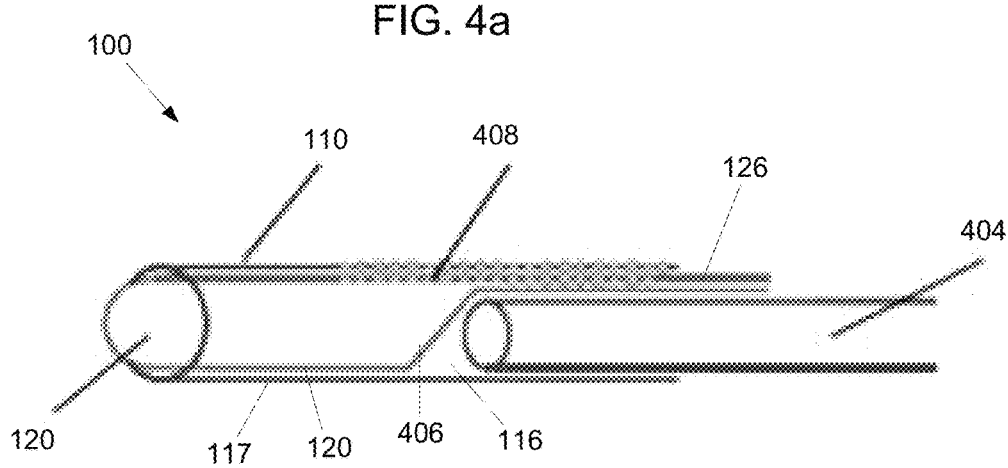

When inflated, the balloon 120 may extend in a substantially straight manner, as shown in FIG. 4B, to aid in extending the sleeve 110 past a site of obstruction. In other words, balloon 120 may have a substantially elongated shape so that, when inflated, balloon 120 expends in a substantially distal direction to aid in extending the distal portion 114 of the sleeve 110 past the site of obstruction.

Figure 5A:
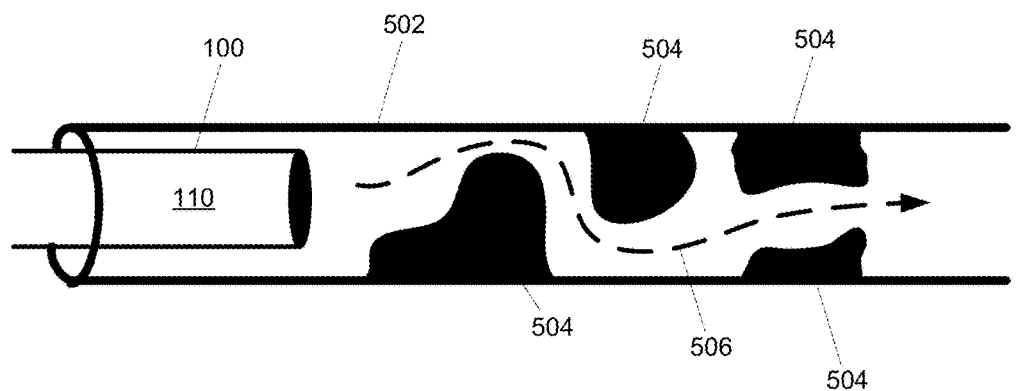
FIGS. 5a-5b illustrate a process for providing access across an area of obstruction in accordance with an embodiment of the present invention.

In one embodiment, as balloon 120 and distal portion 114 of sleeve 110 are designed to be flexible and pliable, balloon 120 and distal portion 114 may act to seek the path of least resistance through a site of obstruction. For example, turning to FIG. 5a, if a vessel 502 is blocked by a site of obstruction 504 (or series of obstructions 504), balloon 120, as it is everting, may seek the easiest path through the site of obstructions 504, as shown by arrow 506, since the fluid introduced into balloon 120 during inflation will tend to push balloon 120 and distal portion 114 of sleeve 110 through the site of obstruction following the path of least resistance. This may allow a user of system 100 to easily, blindly, or automatically find a path or opening through the site of obstruction 504 that would otherwise be difficult or impossible to find by probing the site with a guidewire or other device.

Figure 5B:
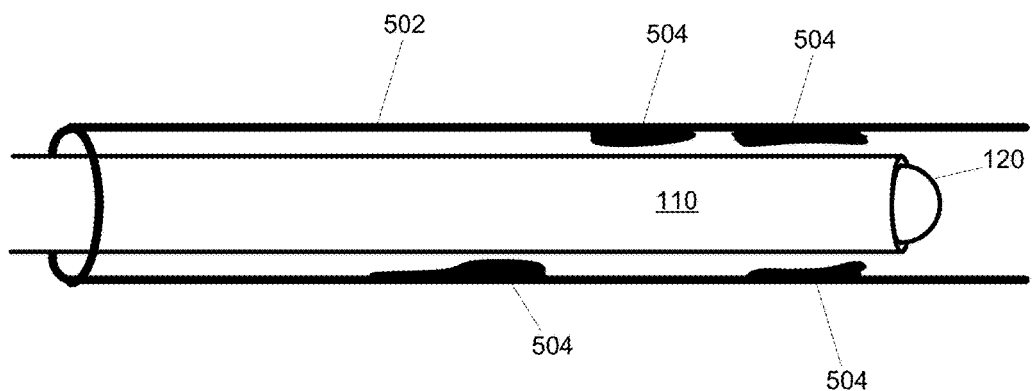

In one embodiment, as balloon 120 is everted through the site of obstruction, the balloon 120 may be designed to dilate or expand any obstruction at the site. As shown in FIG. 5b, as balloon 120 continues to inflate and push through the site of obstruction 504, the balloon 120 may widen the path through the site of obstruction 504 so as to clear a pathway through vessel 502. Of course, as balloon 120 dilates the site of obstruction 504, it may also act to evert sleeve 110 so that sleeve 110 creates a pathway through the vessel and across the site of obstruction 504.

Figure 4C:
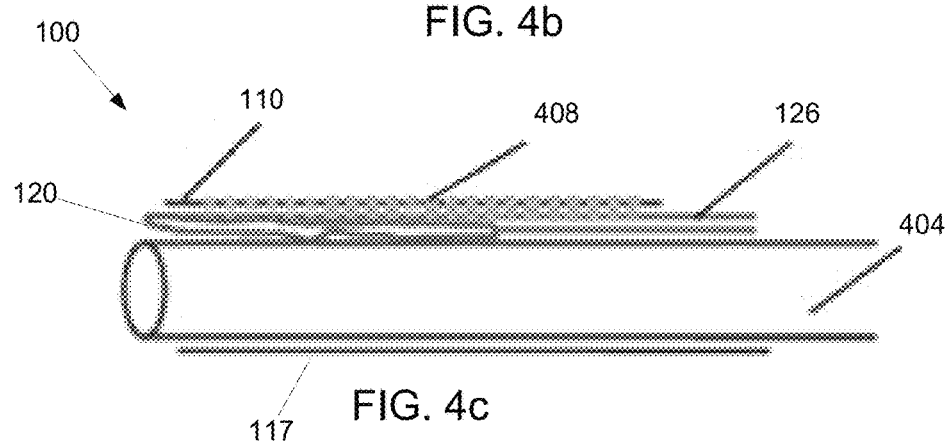

Now referring back to FIG. 4c, following eversion, the balloon 120 may be deflated to allow access along pathway 116 of sleeve 110 so that a device may be directed through sleeve 110. For example, as shown in FIG. 4c, balloon 120, when deflated, may have a smaller profile so that catheter 404 (or another device) may be advanced through sleeve and across the site of obstruction. In one embodiment, deflated balloon 120 may be situated adjacent to the inner wall of sleeve 110 to allow catheter 404 to pass. In other embodiments, balloon 120, when deflated, may be situated in other arrangements, or may be refracted and removed from sleeve 110 before catheter is advanced into or through sleeve 110, so long as catheter 404 can access the site of obstruction and/or a site distal to the obstruction.

In some embodiments, a deflation mechanism (not shown) may deflate balloon 120 by directing fluid out of balloon 120 through lumen 126. As discussed above, deflation mechanism may be a pump, syringe, or other device that can move fluid into and out of balloon 120. In other embodiments, balloon 120 may be designed so that catheter 404 (or another device) deflates balloon 120 by pushing balloon 120 aside as catheter 404 is advanced through sleeve 110. In such a design, balloon 120 may have a tapered wall (e.g. wall 406) so that, as catheter 404 pushes against wall 406, balloon 120 becomes squeezed or compressed between catheter 404 and the inner wall of sleeve 110. The squeezing action may deflate balloon 120 by pushing the fluid out of balloon 120 through lumen 126. Other methods of deflating balloon 120 may also be used. For example, if balloon 120 is no longer needed and/or disposable, a device may be advanced into sleeve to puncture balloon 120 so that it deflates.

To extend the sleeve 110 past an obstruction within a vessel, balloon 120 can be made from a flexible and sufficiently strong material capable of bypassing the obstruction. The balloon 120 should further be made from a sufficiently strong material capable of withstanding a sufficient force causing it to evert. The material of the balloon 120, in another embodiment, may be impermeable to fluids in order to allow the balloon 120 to withstand sufficient pressure. Since the balloon 120 is designed to be inserted within a vessel of a human or animal body, the balloon 120 should be made from a material that is biocompatible. The biocompatibility of the material may help minimize occurrence of adverse reactions due to use of the balloon 120 within a vessel.

The balloon 120 can further be made from any material that can aid in the eversion process. In one embodiment, the balloon 120 can be made from a material that minimizes resistance and friction so as to evert and bypass the obstruction with greater ease. For instance, the balloon 120 can be made from a material that is substantially smooth and/or has a relatively low coefficient of friction. Should it be desired, balloon 120 may further include a coating that can aid in eversion, inflation and deflation, or any other characteristic that may be desirable for the balloon 120. The coating may be applied to the balloon 120 on an inner surface, an outer surface, or a combination thereof.

The length of the balloon 120 may, in an embodiment, vary depending on a variety of characteristics. In certain instances, the length of the balloon 120 may be dependent on the length of the vessel. In other instances, the length of the balloon 120 may vary depending the length of distal portion 114. In yet other instances, the length of the balloon 120 may vary depending upon the length of the possible sites of obstruction. It should be noted that the length of the balloon 120 should permit the balloon 120 to fit within and/or evert the sleeve 110.

Similarly, the balloon 120 may also have any diameter desirable so long as the diameter allows the balloon 120 to fit within the sleeve 110 and the vessel. In some instances, balloon 120 may have a diameter sufficiently large so that, when inflated, it creates a fluid-tight seal against the inner wall of the sleeve. Balloon 120 may also have a diameter sufficiently large so that it can press sleeve 120 against the inner wall of a vessel. In one embodiment, the balloon 120 may have a diameter to allow the balloon 120 to substantially conform to the vessel walls when in an inflated state. However, in the inflated state, the diameter of the balloon 120 may also be smaller than the diameter of the sleeve 110, to minimize the likelihood of rupturing the sleeve 110. Of course, larger or smaller diameters may also be possible.

The balloon 120 may also have any shape desirable so long as the shape allows the balloon 120 to fit within the sleeve 110 and the vessel, and to evert distal end 114. In one embodiment, the balloon 120 may have a substantially tubular shape to allow the balloon 120 to substantially conform to the vessel. Of course, other geometric shapes are also within the scope of the present invention.

Referring again to FIGS. 4a-c, to minimize advancement or retreat of balloon 120 during eversion, the system 100, may include a coupling mechanism 408 that may act to couple a portion of the sleeve 110 to a portion of the balloon 120. The coupling mechanism 150 may be designed to allow eversion of the balloon 120 while minimizing advancement or retreat of the balloon from within sleeve 110. Of course, in some embodiments, coupling mechanism 150 may allow at least some axial movement of balloon 120 during eversion, if desired. The coupling mechanism 150 may be any mechanism capable of securely coupling the balloon 120 and the sleeve 110. For instance, the coupling mechanism 150 may be glue, tape, velco, clips, or any other commercially available mechanism. In other embodiments, coupling mechanism 150 may be a mechanism that increases friction between balloon 120 and sleeve 110. For example, coupling mechanism may be a rough or perforated section of balloon 120 and/or sleeve 110 that creates friction when balloon 120 is inflated and pressed against sleeve 110.

Once sleeve 110 has been everted, sleeve 110 may provide a pathway 117 to permit an object, such as catheter 404, to be delivered across a site of obstruction. The pathway 116, in one embodiment, may extend across juncture 117 between distal end 114 and the remainder of sleeve 110 so that catheter 404 can access the site of obstruction, or access areas distal to the site of obstruction. To provide access across a site of obstruction, catheter 404, or another device, may be advanced along pathway 116 of the sleeve 110 toward the distal portion 114 of sleeve 110. In an embodiment, catheter 404 may be designed to provide sufficient structural integrity to sleeve 110 along its length, so as to minimize collapse, folding, or compaction of sleeve 110. In one embodiment, catheter 404 may be protected by the sleeve 110 as catheter 404 is advanced forward through the vessel, as shown in FIG. 4c. In an embodiment, catheter 404 may be any commercially available catheter, so long as it can be advanced along pathway 116 of sleeve 110. For instance, the catheter 404 may be a therapeutic catheter for delivering, for example, an intravascular stent, or a balloon catheter for angioplasty.

The present invention can be deployed, in accordance with one embodiment, using a gastroscope (not shown). The gastroscope may help guide the system 100 through the vessel to a site of interest. In an embodiment, the gastroscope may be provided with a body positioning designed to be situated about the sleeve 110.

Looking now at FIGS. 6a-c, in other embodiments, the system 100 of the present invention may be designed to allow a guidewire (e.g. guidewire 602) to help guide and direct sleeve 110 through the vessel. In some embodiments, the guidewire may be designed to push the system 110 through a vessel to a site of interest. In such a design, system 100 may include a pocket or slot 118 (see FIG. 1) on its surface that can accommodate an end of guidewire 602. Guidewire 602 may be positioned within slot 118 so that, as guidewire 602 advances through vessel 604, guidewire 602 pushes sleeve 110 through vessel 604 to the site of obstruction 606. In another embodiment, slot 118 may allow sleeve 110 to slide along the length of guidewire 602. In such an embodiment, guidewire 602 may first be advanced into vessel 604 to the site of obstruction 606 (as in FIG. 6a), then sleeve 110 may be advanced along the length of guidewire 602 until sleeve 110 is positioned adjacent to the site of obstruction 606.

The guidewire 602, in an embodiment, may further be capable of positioning sleeve 110 adjacent to site of obstruction 606 so that the balloon 120 can evert sleeve 110 across the site of obstruction 606. It should be noted that while the guidewire 602 can be positioned in any manner to allow guidance of the sleeve 110, its design should minimize any obstructions of the balloon 120 and the sleeve 110 during eversion. In other words, guidewire 602 should be positioned so that it does not impede the eversion of distal end 114. In some embodiments, guidewires such as those described in U.S. Provisional Patent Application 61/435,517 (filed Jan. 24, 2011; incorporated herein by reference in its entirety), can be used to guide sleeve 110 to the site of obstruction 606. In another embodiment, the guidewire 602 may be any guidewire that is commercially available.

In another embodiment, the sleeve 110 may be used in conjunction with guidewire 602 so as to facilitate delivery of guidewire 602 across the site of obstruction 606. In such an embodiment, distal end 114 of sleeve 110 may be everted to provide a pathway 116 across the site of obstruction 606. Guidewire 602 may then be advanced through pathway 116 and across the site of obstruction 606. Subsequently, sleeve 110 may be removed, leaving guidewire 602 in place across the site of obstruction 606 so that guidewire 602 may be used as a track for advancement of other devices to or through the site.

In operation, to prepare the system 100 for insertion into the body, a balloon 120 may be positioned within a sleeve 110. Both the distal portion 114 of the sleeve 110 and a distal end of the balloon 120 can then be inverted so that the distal portion 114 of sleeve 110 is folded into the remainder of the sleeve. In some instances, balloon 120 may be inverted so as to create a pocket 402, within which distal portion 114 may sit. A catheter 404 may also be placed into the sleeve 110.

Once loaded, the system 100 may be inserted into a vessel in the body and advanced along the vessel 604 to a site of obstruction 606, as shown in FIG. 6a. Once at the site of obstruction 606, balloon 120 may be inflated so as to evert distal portion 114 and deliver it across the site of obstruction 606. Inflation of balloon 120 may require the direction of pressurized fluid into balloon 120 via a lumen 126 and/or an inflation port. As balloon 120 is inflated, it may push and evert the distal portion 114 of sleeve 110 from within sleeve 110 across the site of obstruction 606, as shown in FIG. 6b. In some instances, balloon 120 may also blindly or automatically seek a path through the site of obstruction 606 as it is inflated, as described above. Inflation can also open or widen a path through the site of obstruction 606 by causing balloon 120 to dilate the site. Following eversion, balloon 120 may be deflated and/or removed, and catheter 404 may be advanced through pathway 116 to access the site of obstruction, or an area distal to the site of obstruction, as shown in FIG. 6c.

Although described as proving access across a site of obstruction within a vessel within a body, the invention can provide access across other sites of obstruction as well. For example, the invention can be used to provide access across an obstruction in a cavity or other type of opening. Furthermore, the invention is not limited to use within the medical field. The sleeve can, for instance, be delivered across an obstruction in a cave or other type of passage. Additionally, since the balloon may be designed to seek the path of least resistance, as described above, the invention may be used to seek out hidden or unknown pathways through various sites of obstruction. In other embodiments, the invention may be equipped with an object or device to be delivered across a site of obstruction. In such an embodiment, the device may be situated on the distal portion 114 of sleeve 110, or on a distal end of balloon 120, so that as sleeve 110 everts across and balloon 120 extends through the site of obstruction, the object is delivered to an area distal to the site of obstruction.

While the invention has been described in connection with specific embodiments, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

What is claimed is:

1. A method of providing access across a site of obstruction, the method comprising:
    positioning an inverted, distal portion of a sleeve adjacent to a site of obstruction;
    inflating a balloon from a position in which a length of the balloon is situated entirely within a length of a remaining portion of the sleeve such that the balloon moves the distal portion from an inverted position to an everted position so the distal portion extends across the site of obstruction; and
    deflating the balloon after eversion so as to provide access across the site of obstruction via a pathway through the sleeve, the pathway extending alongside the deflated balloon, across a juncture between the distal portion and the remaining portion of the sleeve and through a distal end of the distal portion.

2. A method as set forth in claim 1, wherein the step of positioning includes advancing the distal portion of the sleeve through a vessel to the site of the site of obstruction.

3. A method as set forth in claim 1, wherein the step of inflating includes allowing the balloon, during in inflation, to seek a path of least resistance through the site of obstruction.

4. A method as set forth in claim 1, wherein the step of inflating includes dilating the site of obstruction with the balloon as the balloon is inflated.

5. A method as set forth in claim 1, wherein the step of inflating includes pressing the sleeve against the inner wall of a vessel to minimize movement of the sleeve during eversion.

6. A method as set forth in claim 1, further comprising advancing a device through the pathway and across the site of obstruction to access across the site of obstruction.

7. A method of providing access across a site of obstruction, the method comprising:
    positioning an inverted, distal portion of a sleeve adjacent to a site of obstruction;
    inflating a balloon situated within the sleeve such that the balloon moves the distal portion from an inverted position to an everted position so the distal portion extends across the site of obstruction, a coupling mechanism securely coupling the balloon to an inner surface of a remaining portion of the sleeve so as to minimize advancement or retreat of the balloon within the remaining portion of the sleeve during eversion of the balloon; and
    deflating the balloon after eversion so as to provide access across the site of obstruction via a pathway extending through the sleeve, the pathway extending alongside the deflated balloon, and across a juncture between the distal portion and a remaining portion of the sleeve and through a distal end of the distal portion.

* * * * *